United States Patent [19]
Grant

[11] Patent Number: 5,811,257
[45] Date of Patent: Sep. 22, 1998

[54] DETECTION APPARATUS

[75] Inventor: Peter Leonard Grant, Cambridgeshire, United Kingdom

[73] Assignee: Celsis International, P.L.C., Cambridge, United Kingdom

[21] Appl. No.: 557,112

[22] PCT Filed: May 27, 1994

[86] PCT No.: PCT/GB94/01162

§ 371 Date: Nov. 30, 1995

§ 102(e) Date: Nov. 30, 1995

[87] PCT Pub. No.: WO94/28110

PCT Pub. Date: Dec. 8, 1994

[30] Foreign Application Priority Data

Jun. 1, 1993 [GB] United Kingdom .................. 9311242

[51] Int. Cl.[6] ...................................................... C12M 3/00
[52] U.S. Cl. ........................ 435/30; 435/288.6; 422/101; 436/178; 210/767; 210/800; 210/802; 210/348; 216/433.1; 216/434
[58] Field of Search .............................. 435/288.1, 288.2, 435/288.5, 288.6, 30; 422/101; 436/178; 210/767, 800, 802, 348, 433.1, 434

[56] References Cited

U.S. PATENT DOCUMENTS

| 4,829,005 | 5/1989 | Friedmann et al. | 435/296 |
| 5,358,690 | 10/1994 | Guirguis | 422/58 |

FOREIGN PATENT DOCUMENTS

| 9013624 | 11/1990 | WIPO | C12M 1/12 |
| 9118653 | 12/1991 | WIPO | C12M 1/12 |
| 9217261 | 10/1992 | WIPO | B01D 25/02 |

Primary Examiner—David A. Redding
Attorney, Agent, or Firm—Saliwanchik, Lloyd & Saliwanchik

[57] ABSTRACT

The subject invention pertains to an assay device suitable for use in testing samples for the presence of microorganisms. The assay device of the subject invention comprises a housing having two chambers therewithin, each chamber being partially defined by a first filter material and each having a liquid inlet, the device also comprising means for holding the first material in a first or second position, respectively, such that the chambers are either separate or in communication. This arrangement allows assays to be made more accurately, since material that is otherwise retained in the corners of the assay chamber can be simply washed away.

10 Claims, 1 Drawing Sheet

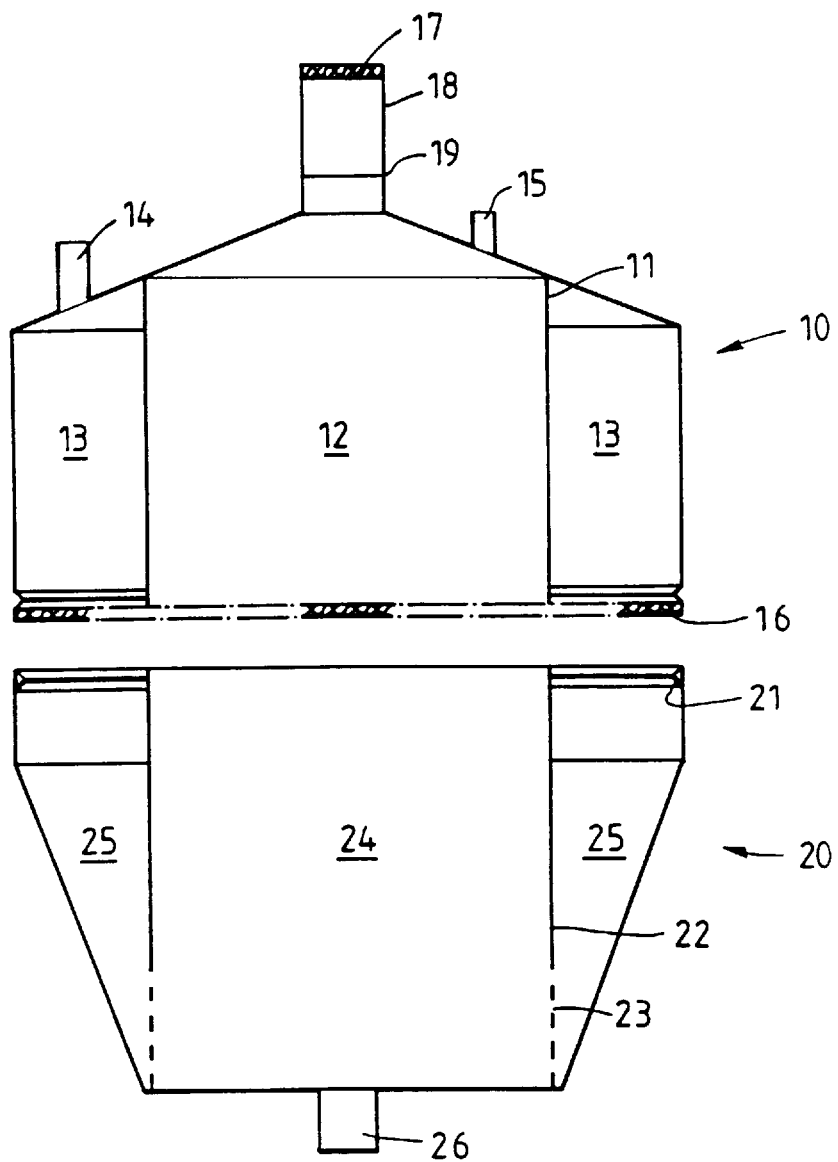

DETECTION APPARATUS

FIELD OF THE INVENTION

This invention relates to apparatus suitable for use in testing liquid samples for the presence of microorganisms.

BACKGROUND OF THE INVENTION

Apparatus for the detection of microorganisms in liquid samples is known, the use of which involves the introduction of the sample, optionally followed by wash liquid, and then growth medium, to encourage the organism to multiply. In some cases, the sample may be an antibiotic which, if residual material remains, can inhibit the growth of organisms thereby giving false negative results. The difficulty encountered with such apparatus is that residual sample may become trapped in corners of the apparatus and is difficult to remove.

SUMMARY OF THE INVENTION

The present invention provides simple apparatus, suitable for manual use, which can obviate the problem described above and provide for both biological detection and optimised sterility testing. The novel assay device comprises a housing having two chambers therewithin, both chambers being partially defined by a filter material and each having a liquid inlet, the device comprising also means for holding the filter material in a first or second position, respectively, such that the chambers are either separate or in communication.

In use of the apparatus, the region of contact between the filter material and the chamber division, where residual sample may collect while the said means is maintained in the first position, can be simply and effectively washed by selecting the second position. A further advantage of the novel apparatus is that is it well adapted to the use of sensitive bioluminescence assays, and by contrast with conventional turbidity observation.

BRIEF DESCRIPTION OF THE DRAWINGS

FIG. 1 shows a schematic sectional view of a device embodying the present invention.

DESCRIPTION OF THE INVENTION

The invention will now be described by way of example only with reference to FIG. 1, which is a schematic sectional view of a device embodying the present invention.

FIG. 1 shows a generally cylindrical housing 10 having an internal cylindrical wall 11 that effectively divides the housing into respective cylindrical and annular chambers 12, 13. These chambers have respective liquid inlets 14, 15 (although one inlet may be replaced by an internal communication), and are partially defined by a common filter material 16.

FIG. 1 shows also a complementary generally cylindrical part 20 that is engageable with the housing 10, suitably by means of complementary circumferential engagement means 21, e.g., a snap-fit or threaded engagement (if the latter, the housing 10 and part 20 may be held together at all times, in engagement to a greater or lesser degree defining the first and second positions of the filter material 16, as discussed below). The part 20 comprises an internal generally cylindrical wall 22 corresponding to wall 11, and including perforations 23 such that the respective generally cylindrical and annular volumes 24, 25 are in communication. The part 20 also includes a liquid outlet 26.

In use, the housing 10 and part 20 are firmly engaged, such that their respective walls 11 and 22 are substantially in contact, and may compress the filter material 16 therebetween. In this "first" position, the chambers 12 and 13 are separate.

Sample is now introduced through inlet 15 into the chamber 12, and liquid is allowed or caused to drain through the filter material 16 and then out of the device through the outlet 26.

Sample may have collected at the interface of the wall 11 and the filter material 16, and possibly beyond the wall 11. However, the filter material can now be effectively washed by moving or partially disengaging the part 20, so that the filter material 16 is no longer held in close contact with the wall 11, i.e., in the "second position" and introducing a wash material through inlet 14.

A growth medium may now be introduced through the inlet 15 into the chamber 12, to allow the growth of microorganisms retained on the filter material 16 unless that is inhibited by antibiotic. Following growth, liquid can be removed through the outlet 26.

According to a particularly preferred embodiment of the invention, the inlets 14 and 15 are closed, the housing 10 inverted, and the growth medium is washed into contact with a second filter material 17 that partially defines a member 18 that can be separated from the housing 10, usually by means of a frangible, male-female or other connection at 19. This separable member 18 is suitably in the form of a cuvette that can be introduced directly into a suitable analytical instrument, or retained by the user for future analysis. By the provision of several members 18 that can be releasably connected to the housing 10, the novel device can be used for multiple assays.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. An assay device comprising a housing partially defined by a first filter material and having two chambers therewithin, said chambers forming an integral part of said housing and each chamber being partially defined by said first filter material and each of said chambers having a liquid inlet, the device also comprising means for holding said filter material in a first or second position, respectively, such that said chambers are either separate or in communication.

2. The device according to claim 1, wherein said filter holding means comprises a structure engageable with said housing and providing said filter holding means according to the degree of engagement.

3. The device according to claim 1, in which one chamber is surrounded by the other chamber.

4. The device according to claim 1, which additionally comprises a separable member partially defined by a second filter material and in communication with one of said chambers.

5. A method for retaining an analyte present in a liquid sample, which comprises the steps of:

(a) introducing the sample into one of said chambers of a device according to claim 1 and through said first filter material in the first position; and (b) introducing a wash liquid into the other chamber, when said first filter material is in the second position.

6. The method according to claim 5, in wherein said method the device is as defined in claim 4, which additionally comprises the steps of inverting said device and separating said separable member, when desired.

7. The method according to claim 5, wherein the analyte is a microorganism.

8. The method according to claim 7, wherein said method additionally comprises the step of introducing a growth medium into the chamber of said device.

9. The method according to claim 6, wherein the analyte is a microorganism.

10. The device according to claim 3, wherein said other chamber is annular.

* * * * *

UNITED STATES PATENT AND TRADEMARK OFFICE
CERTIFICATE OF CORRECTION

PATENT NO. : 5,811,257

DATED : September 22, 1998

INVENTOR(S) : Peter Leonard Grant

It is certified that error appears in the above-identified patent and that said Letters Patent is hereby corrected as shown below:

*In the Claims*

Column 3, lines 3-4:

"6. The method according to claim 5, in wherein said method the device is as defined in claim 4, which additionally comprises the steps of inverting said device and separating said separable member, when desired."

should read

--6. The method according to claim 5, wherein said device is as defined in claim 4, wherein said method additionally comprises the steps of inverting said device and separating said separable member, when desired.--

Signed and Sealed this

Tenth Day of October, 2000

*Attest:*

Q. TODD DICKINSON

*Attesting Officer*     *Director of Patents and Trademarks*